(12) United States Patent
Zander et al.

(10) Patent No.: US 7,549,994 B2
(45) Date of Patent: *Jun. 23, 2009

(54) TARGETING DEVICE FOR A LOCKING NAIL

(75) Inventors: Nils Zander, Eckernförde (DE); Axel Cremer, Fahrenkrog (DE)

(73) Assignee: Stryker Trauma GmbH, Schönkirchen (DE)

( * ) Notice: Subject to any disclaimer, the term of this patent is extended or adjusted under 35 U.S.C. 154(b) by 807 days.

This patent is subject to a terminal disclaimer.

(21) Appl. No.: 10/694,479

(22) Filed: Oct. 27, 2003

(65) Prior Publication Data

US 2004/0138671 A1 Jul. 15, 2004

(30) Foreign Application Priority Data

Nov. 2, 2002 (DE) ................. 202 16 857

(51) Int. Cl.
*A61B 17/58* (2006.01)
*A61B 17/60* (2006.01)
*A61F 2/00* (2006.01)

(52) U.S. Cl. ........................................ 606/99

(58) Field of Classification Search .......... 606/53, 606/54, 59, 60, 62, 63, 64, 67, 86, 96, 97, 606/98, 99

See application file for complete search history.

(56) References Cited

U.S. PATENT DOCUMENTS

| | | |
|---|---|---|
| 4,103,683 A | 8/1978 | Neufeld |
| 4,913,137 A | 4/1990 | Azer et al. |
| 5,234,434 A * | 8/1993 | Goble et al. ............... 606/96 |
| 5,281,224 A | 1/1994 | Faccioli et al. |
| 5,354,300 A | 10/1994 | Goble et al. |
| 5,478,341 A * | 12/1995 | Cook et al. ............... 606/62 |
| 5,741,084 A * | 4/1998 | Del Rio et al. ............ 403/349 |
| 5,928,235 A | 7/1999 | Friedl |
| 6,010,505 A | 1/2000 | Asche et al. |
| 6,039,739 A * | 3/2000 | Simon ...................... 606/64 |
| 6,039,742 A * | 3/2000 | Krettek et al. ............. 606/96 |
| 7,144,399 B2 * | 12/2006 | Hayes et al. .............. 606/98 |
| 7,232,443 B2 * | 6/2007 | Zander et al. ............. 606/99 |

* cited by examiner

*Primary Examiner*—Anu Ramana
(74) *Attorney, Agent, or Firm*—Lerner, David, Littenberg, Krumholz & Mentlik, LLP

(57) ABSTRACT

A targeting system has a targeting device for a locking nail which is proximally provided with cross-bores the axes of which are disposed in an offset relationship from each other by predetermined distances and/or by predetermined angles. The apparatus has a target arm having at least one target bore and a holding device mounted on the target arm to engage the distal end of the nail. The holding device has a reception bore in which a retaining or locating bar is guided. The locating bar extends in parallel with the target arm and generally perpendicular to the cross-bore. The locating bar has fasteners to fix it to the nail. The retaining bar has several recesses in the area of the reception bore. The reception bore has associated therewith a radially movable locking element or detent element which can be moved into engagement with one of the recesses by use of a handle to locate the axial and rotational positions of the retaining bar in the reception bore. The arrangement of the recesses is such that the target bore of the arm is aligned with a cross-bore of the nail when the locking element engages a recess. The handle has a cam device which signals whether the locking element is in engagement with a recess or is not in engagement therewith.

21 Claims, 3 Drawing Sheets

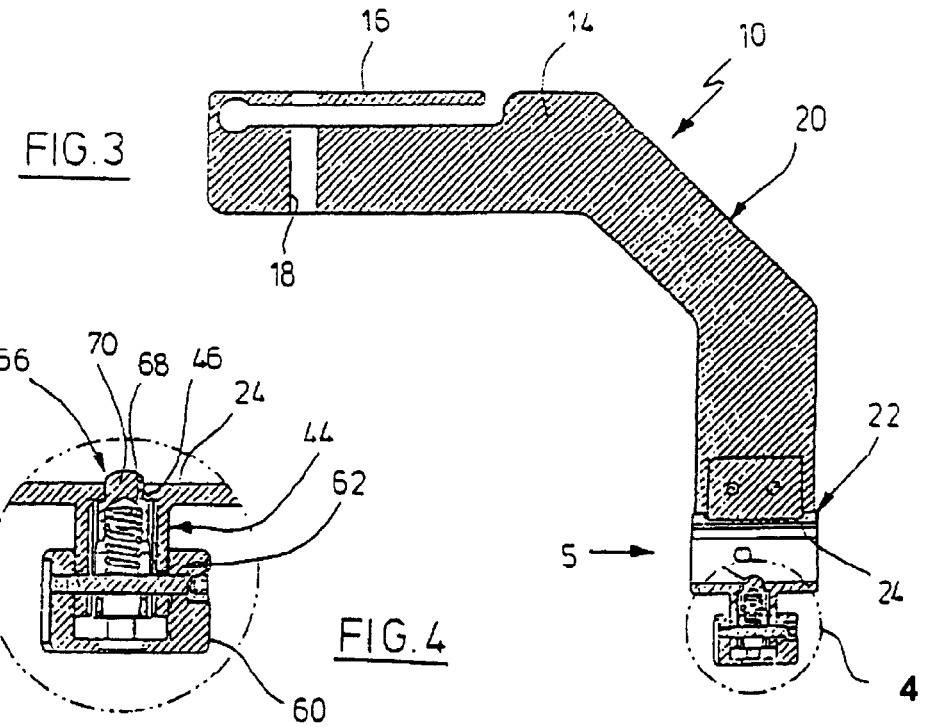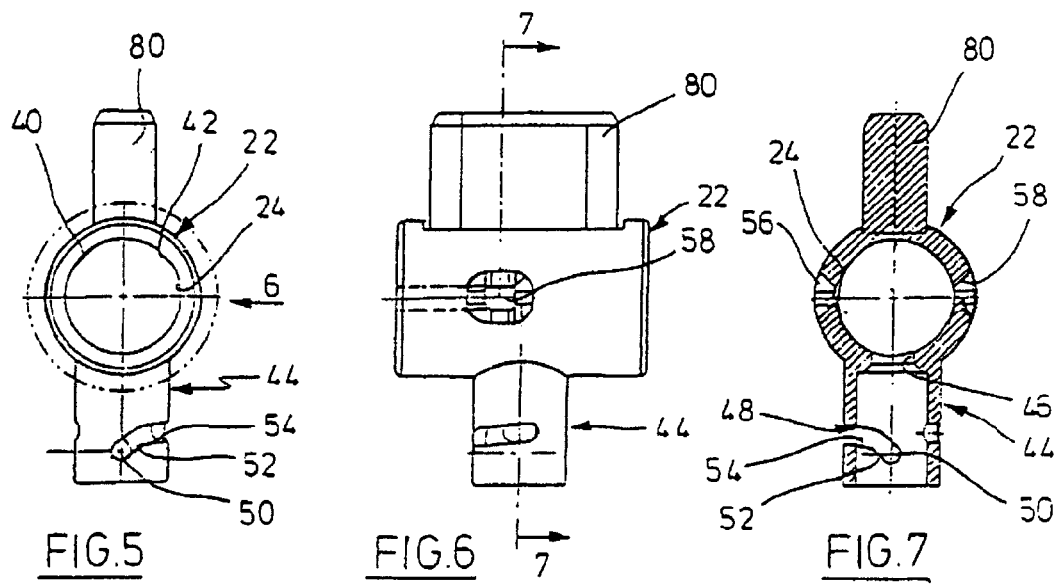

TARGETING DEVICE FOR A LOCKING NAIL

BACKGROUND OF THE INVENTION

The invention relates to a targeting apparatus for a locking nail.

The targeting apparatus of the present invention is particularly suited for supracondylar nails. Such a nail is shown in U.S. Pat. No. 6,010,505, the teachings of which are incorporated herein by reference. As is known, supracondylar nails are driven into the bony canal via the end of the distal femur. They serve for taking care of fractures in the condylar range of the femur. A nail of this type is designed as a locking nail, i.e. it is provided with cross-bores through which locking screws are passed to securely anchor the nail in the femur. A targeting apparatus is required to locate the cross-bores of a locking nail.

One type of targeting apparatus for locking nails is the one where the targeting apparatus is placed onto one end of the locking nail. Here, the targeting apparatus also serves as a hammering instrument to drive the nail into the femoral canal. On its target arm, the target apparatus has at least one target bore which is aligned with a bore in the nail shank. After the nail is knocked or hammered in, a hole is drilled into the bone via the target bore before the locking screws are threaded in. Such a targeting device is shown in U.S. Pat. No. 6,039,739.

It is known for locking nails to have the cross-bores arranged at different angles and distances. It is further known to offset to axes of the cross-bores by predetermined angles in the circumferential direction of the nail. Furthermore, it is known to provide nails of different lengths with their cross-bores having different distances from the distal end. Unless particular provisions are made, a separate targeting apparatus would be required for each of the different nails. This results in an unacceptably large number of targeting devices and related cost when a large number of such nails are provided.

SUMMARY OF THE INVENTION

Therefore, it is the object of the invention to provide a target apparatus for locking nails which enables the insertion of nails having different lengths and differently arranged cross-bores.

In the targeting device of the present invention, a holding device which joins the locking nail to the targeting apparatus has a reception bore which, in turn, receives a retaining bar. The retaining bar which is arranged in the reception bore extends nearly in parallel with a targeting arm in which there is at least one target bore. A target apparatus of this type is described in co-pending U.S. application Ser. No. 10/391,896 filed on Mar. 19, 2003. The retaining bar has recesses in the area in which it is located within the target bore. The recesses, for example, can be engaged by a locking pin which is movable radially to the axis of the reception bore. Thus, the pin locates both the axial position and rotational position of the retaining bar. The retaining bar has a coupling element for engaging the associated end of the locking nail. These commonly include a threaded pin which is screwed into the end of the nail, extends through the hollow retaining bar, and is subjected to a tensile stress by means of a nut at the other end in order that the nail and retaining pin be firmly pulled against each other. Moreover, interacting locating element of the nail and retaining pin locate a predetermined rotational position of these components with respect to each other.

The locking pin is actuated by a handle to optionally bring about an engagement with a recess or to unlock the locking pin. The position of the recesses in the retaining pin is such as to orient the target bore in the target arm to a crossbore of the nail when the locking nail is in a recess.

A manufacturer of locking nails having different dimensions or different arrangements of the cross-bores will naturally produce only one set of such nails. This set is designed to cover all treatment cases that normally occur. Consequently, the retaining bar only needs to have the maximum number of recesses which match with the cross-bores of the individual nails of the set. Of course, it is also possible to provide a plurality of retaining bars which match with only certain locking nails.

According to the present invention, the handle has associated therewith, a device which signals whether the locking element or pin engages a recess. This allows the surgeon to recognize whether there is a predetermined connection between the target apparatus and the nail. This prevents any faulty operation.

An aspect of the invention provides that the handle is rotatably supported on a radial outer lug of a retaining portion exhibiting the reception bore. This handle is preferably defined by a rotary knob or the like. The handle actuates a radial portion which interacts with a cam surface in such a way that if the handle is rotated from an initial position in which the locking element is in its unlocking position the locking element is moved into the reception bore in one direction of rotation. The cam surface joining the unlocking position has a first cam surface portion which is joined by another cam surface portion. The engagement between the radial portion and the second cam surface takes place in a self-locking manner. The handle or radial portion is acted on by a spring in the direction of the unlocking position. Therefore, if the radial portion is in the first cam surface portion it will automatically move the handle back to the unlocking position when it is released while also bringing the locking element into the release position. On the contrary, if the radial portion is in the second cam surface portion there is a self-locking situation and the locked position once set cannot release again by itself.

The function described has the following advantage. When the locking element is outside a recess of the retaining bar the handle can admittedly be rotated by a certain amount, but there is no success in moving the radial portion into the second cam surface portion. The result is that a leap back or springing occurs to the unlocked position. This is what the surgeon can make out immediately. However, when the locking element gets into the recess, the radial portion can be moved into the second cam surface portion and, hence, remains in the locking position.

It is an advantage if the locking element is biased by a spring which makes it easier to discover a recess. An annular groove near the recesses also facilitates its discovery.

According to another aspect of the invention, the radial lug is annularly cylindrical and the cam surface portions are defined by at least one groove in the wall of the radial lug. The handle engages the groove by a radial portion. According to a further aspect of the invention, the radial portion can be defined by a cross-pin which radially extends through the lug and is preferably fixed to the two ends in the handle. Two equal grooves are required in the lug, for this purpose. At the same time, the cross-pin may extend through a cross-bore of the locking element to shift it in an axial direction.

Another aspect of the invention provides that the reception bore is formed in an annularly cylindrical component which is adapted to be located on the target arm by means of a radial outer tongue. For example, the targeting arm may be integrally formed from a suitable plastic material or metal while the cylindrical component with the tongue is made of a different metal.

According to a further aspect of the invention, the cylindrical component has at least one window through which the retaining bar can be seen. The retaining bar can have placed thereon numbers or the like which appear in the window when the retaining bar has been located in a certain position.

These and other objects of the invention are provided for in a targeting apparatus for a locking nail of the type having cross-bores, the axes of which are disposed in an offset relationship from each other with respect to the longitudinal axis of the nail. The angular offset may either be in a circumferential plane or in a proximal/distal plane with respect to the nail axis and the cross-bores may also be spaced in the proximal/distal direction. The targeting apparatus has at least one screw target bore and a reception bore for a holding device to retain a first end of the nail. The reception bore is provided in which a retaining bar is guided, which bar extends parallel to the targeting arm. The retaining bar has a fastener to fix the nail to an adjacent end of the bore. The retaining bar has several recesses in the area of the reception bore and the reception bore includes a moveable locking element which can be caused to engage one of the recesses in the bar by use of a handle. The locking element locates and fixes the axial and rotational positions of the retaining bar in the reception bore. The recesses are arranged such that the target bore in the targeting arm is aligned with a cross-bore of the nail and the locking element engages a recess. The handle includes a spring loaded knob for indicating whether the locking element is in engagement with the recess or is out of engagement therewith. While, in the preferred embodiment, a spring loaded knob is utilized, any structure which signals the positive engagement between the locking element, such as a pin, and the recess, can be utilized.

Preferably, the handle is rotatably supported on a radially extended outer lug or tube of a retaining portion including the reception bore. The handle actuates a radial portion or pin which engages with a cam surface on the lug such that if the handle is rotated from an initial position in which the locking element is in its unlocked position, the locking element is moved into the reception bore by a pre-determined direction of rotation of the handle. This is accomplished by a cam surface having a first cam surface portion joining the unlocked position and a second cam surface portion joining the first cam surface portion. Thus, the engagement of the radial portion and the second cam surface portion takes place in a self-locking manner and the handle or the radial portion is biased by a spring in the direction of the unlocked position. As indicated, the radial lug can be tubular and is preferably annularly cylindrical and the cam surfaces are defined by a groove in the lug or tube wall and the radial portion connected to the handle preferably is a pin or cam follower engaging the groove. In the preferred embodiment, the locking pin has an axial bore in which in a helical spring is arranged having one end supported on the cross-bore. The cross-pin extends through a cross-bore of the locking pin. The reception bore is defined by an annularly cylindrical component which is adapted to be located in a recess of the targeting arm by means of a radial outer tongue but can be affixed to the targeting arm by any convenient manner. In the preferred embodiment, the retaining bore has at least one window through which the retaining bar can be seen. In the preferred embodiment, the reception bore includes angled flats or prismatic surfaces which are mounted within the bore or on the side opposite the locking element and against which the retaining bar is pressed by the locking element. In the preferred embodiment, the recesses in the retaining bar include annular grooves by which the locking element can be brought into engagement with the recesses.

The targeting arm has at least one guide bore alignable with a cross-bore for guiding a drill for inserting a cross-locking screw. The arm has a bushing in the reception bore extending along an axis generally perpendicular to this reception bore axis. The targeting device includes a targeting arm positioning rod or bar rotatably and slidably mounted within a bore of the bushing with the rod fixedly mounted on an end of the intramedullary nail. The positioning rod includes a plurality of offset detents corresponding to the locations of the cross-bores of the nail. These detents are usually recesses formed on the outer circumference of the rod. A detent element is mounted on the bushing and is selectively moveable into and out of engagement with the recesses on the positioning rod upon axial and/or rotational movement of the rod with respect to the bushing aligning the recesses with the detent element and axial movement of the element. The spring biased detent element is axially moveable from a first position in the bushing bore wherein the detent element extends only partially into the bushing bore and into each detent recess to a second position in the bore in which the detent element extends fully into the recess. In order to accomplish this, the bushing has an actuator handle mounted on an outer circumferential surface thereof, which handle engages the detent element on the bushing. The handle has a pin which engages cam surfaces to axially move the detent element from the first position wherein the detent element is only in the partially inserted first position to the second position wherein the bushing is in the fully inserted second position.

BRIEF DESCRIPTION OF THE DRAWINGS

The invention will be described in more detail below with reference to an embodiment shown in the drawings.

FIG. 3 is a longitudinal section through the component of FIG. 2;

FIG. 4 is an enlarged view of the encircled portion 4 of FIG. 3;

FIG. 5 is a side view of a component of the target apparatus of FIG. 3 in the direction of arrow 5;

FIG. 6 is a side view of the component of FIG. 5 in the direction of arrow 6;

FIG. 7 is a section through the representation of FIG. 6 taken along line 7-7;

FIG. 8 is an angled view of a groove of the component of FIGS. 5 through 7;

DETAILED DESCRIPTION

Figure 1:
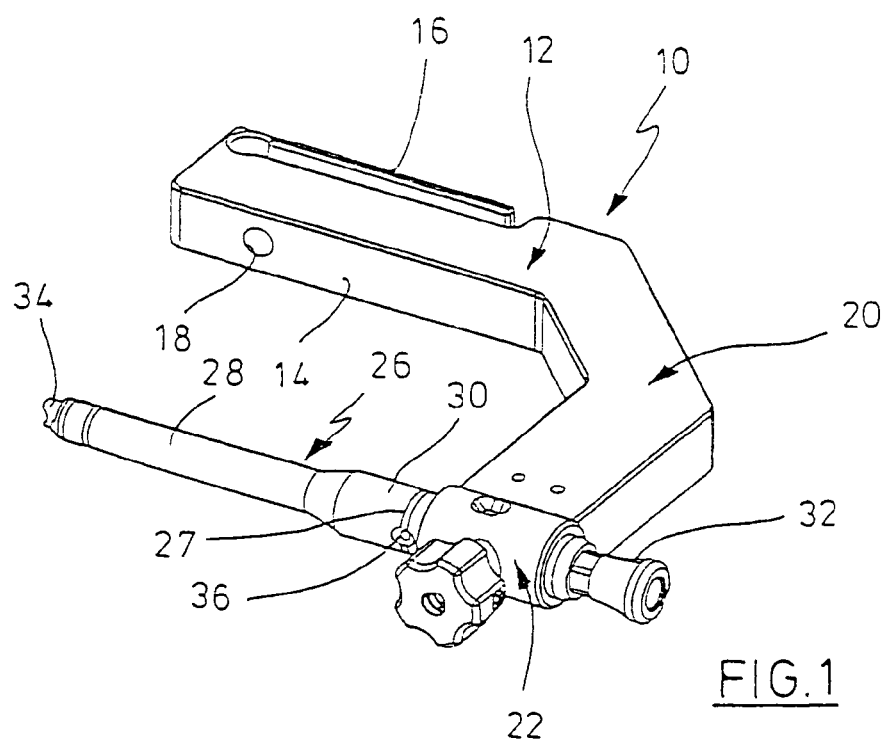
FIG. 1 is a perspective view of a targeting apparatus according to the invention.
Figure 2:
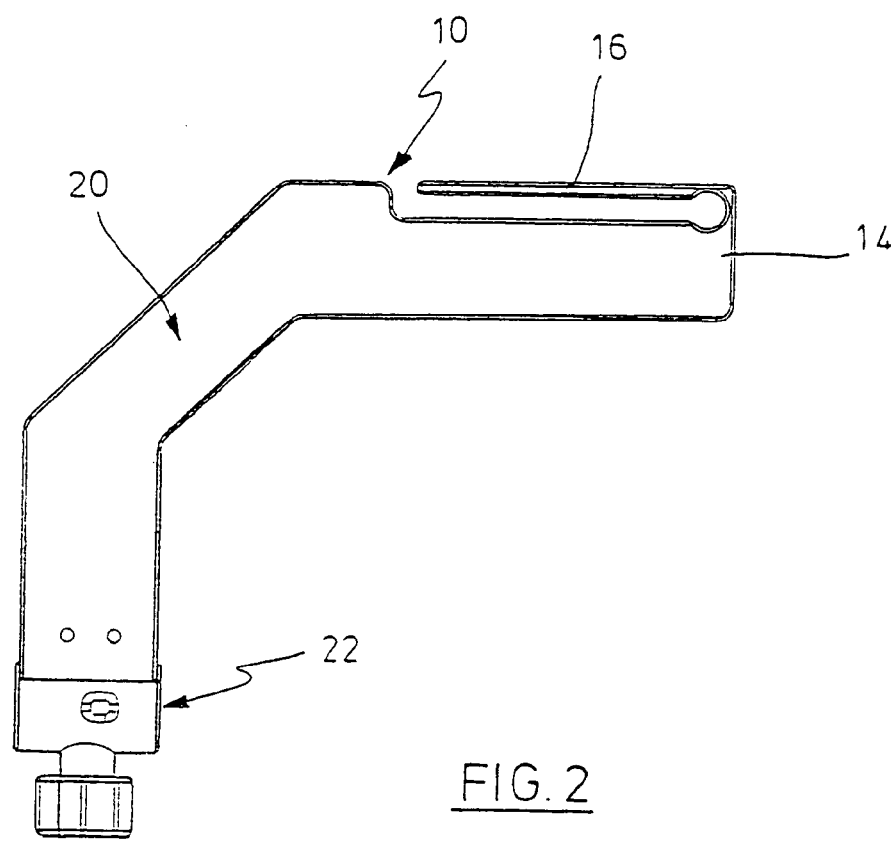
FIG. 2 is a side view of the targeting apparatus of FIG. 1 with no retaining bar.
Figure 9:
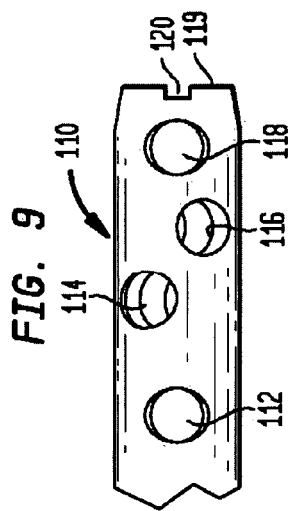
FIG. 9 is the distal end of a locking nail.
Figure 10:
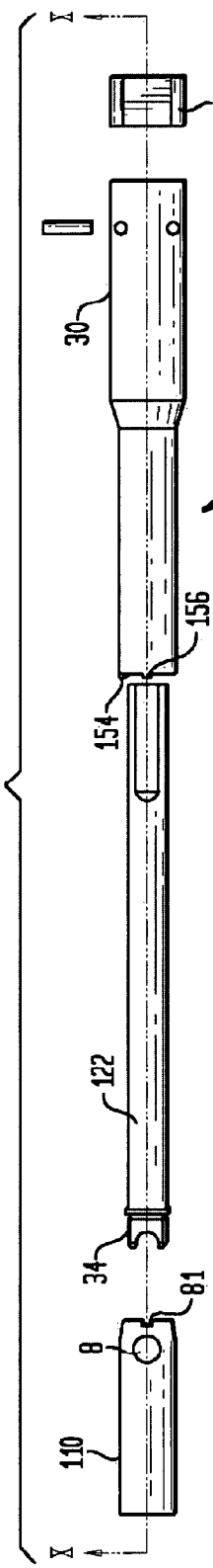
FIG. 10 is an exploded view of the nail retention screw and a joining sleeve.
Figure 11:
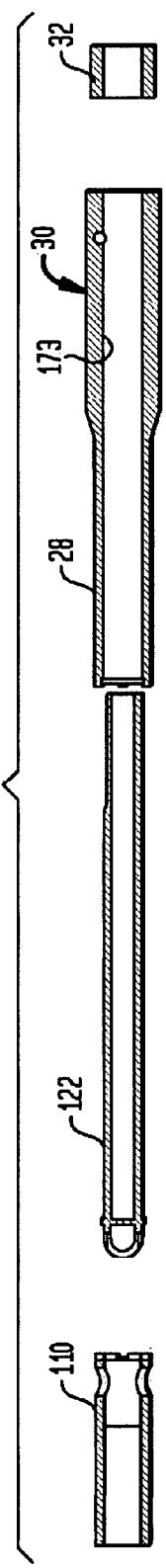
FIG. 11 is a sectional view along lines X-C of FIG. 10.

Referring to FIGS. 1 through 3, there is shown the targeting apparatus of the present invention generally designated 10. Device 10 has a target arm 12. Arm 12 has a relatively thick, enlarged portion 14 and a resilient portion 16 which is separated by a slot from the larger portion 14. Both portions 12 and 14 are traversed by a targeting bore 18. The resilient portion 16 enables a pin or targeting sleeve to be introduced into the targeting bore 18 and to be located in a desired position. This principle is well known from U.S. application Ser. No. 10/391,896 filed on Mar. 19, 2003, now U.S. Pat. No. 7,232,443, the disclosure of which is incorporated herein by reference.

In the preferred embodiment, targeting arm 12 is connected to an angled retaining portion 20 at the end of which is mounted an annularly cylindrical portion 22. The cylindrical portion 22 will be explained in more detail below with references to FIGS. 3-7.

The cylindrical portion 22 has a reception bore 24 in which a retaining bar 26 is received. The retaining bar 26 exhibits a first cylindrical portion 28 at the end of which an end of a locking nail, which is not shown, can be mounted in a manner which is depicted in FIGS. 9-12, as is illustrated in U.S. Pat. No. 7,232,443, based on co-pending application Ser. No. 10/391,896. The locking nail 110 may be a supracondylar nail, for example. A larger-diameter cylindrical portion 30 of the retaining bar 26 extends through the reception bore 24 of the cylindrical component 22. In the preferred embodiment, at the other end of the retaining bar 26, a nut 32 is screwed onto a thread of a tension bar 122 and extends through a bore in the hollow retaining bar 26. The front end of the tension bar 122 is shown at 34. End 34 of the tension bar 122 is screwed into a female thread of the locking nail 110 so as to allow it to be tensioned against the left-hand end of the retaining bar 28 in FIG. 1. A location device 154, 156 on the bar 26 and 81 on the nail 110 between the nail 110 and retaining bar 26 also help locate the locking nail 110 in its rotational position relative to the retaining bar 26.

Figure 12:
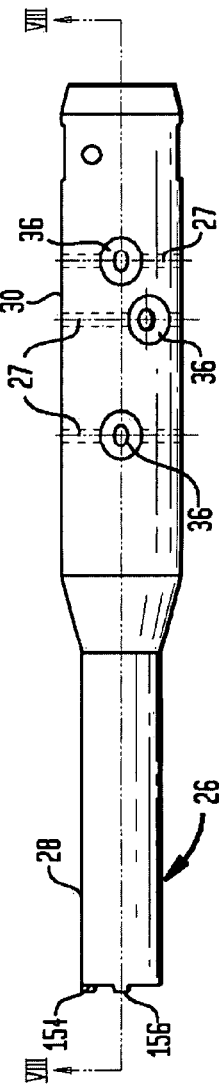
FIG. 12 is a joining sleeve shown in FIGS. 10 and 11.

The cylindrical portion 30 has disposed therein several spaced-apart recesses 36. One is shown at 36 in FIG. 1. It rests on an annular groove 27. FIG. 12 shows a plurality of recesses or detents 36.

The cylindrical component 22 is shown in more detail in FIGS. 5 through 7. In the preferred embodiment, reception bore 24 is not strictly of a circularly cylindrical shape, but that straight surface portions or flats are formed in two positions at 40, 42. In a nearly diametrical opposition to these flat surface portions, the outside of component 22 has mounted thereon a sleeve portion 44 which extends into reception bore 24 via an aperture 46 in cylindrical component 22. As is further evident from FIGS. 5 through 7, the preferred sleeve portion 44 is cylindrical and has two grooves or cam surfaces 48 which are arranged in a diametrically opposed fashion. Grooves or cam surfaces 48 are arranged so as to have one end thereof on diametrically opposite sides of sleeve 44. One end of a groove or cam surface 48 is shown at 50 in FIG. 5. This portion is joined by a first groove or cam surface portion 52 which is inclined towards element 22 at an angle relatively steep. Portion 52 is joined by a second groove or cam surface portion 54 which is relatively flat or at a shallow angle with respect to the longitudinal axis 55 of sleeve 44. Such a groove is shown in FIG. 8 in an enlarged view. In the preferred embodiment, relatively steep groove or cam surface portion 52 has an angle of ascent of about 35°. The groove or cam surface portion 54, which is flatter and circumferentially longer, has an angle of ascent of about 5°.

In FIGS. 6 and 7, it is shown that component 22 has diametrically opposed windows 56, 58 the function of which will be referred to later.

It can be seen from FIG. 4 that a rotary knob 60 is rotatably supported on sleeve portion 44. Rotary knob 60 is diametrically traversed by a driver pin or cross-pin 62 which engages cam portions 52 and 54 and acts as a radial cam follower. Cross-pin 62 extends through grooves 48. Rotary knob 60 is in a differing axial position on sleeve portion 44, which depends on the rotated position of pin 62 in grooves 48.

Within sleeve portion 44, a locking pin 66 is slidably arranged in an axial direction. Pin 66 is hollow in its lower region as shown in FIG. 4. Furthermore, sleeve 44 has a cross-bore through which pin or cam follower 62 extends. Locking pin 66 has an axial bore with a helical spring 68 placed therein. An enlarged locking portion 70 of pin 66 extends into the reception bore 24 through the aperture 46. FIG. 4 shows the position of locking pin 66 in which the locking portion 70 protrudes farthest radially into reception bore 24. Any further axial movement is limited by an outer shoulder of pin 66 (not shown) and bears on the border of aperture 46.

In the unlocked position of the arrangement described, cross-pin or cam follower 62 is in the end regions of grooves or cam surfaces 48 which are designated 50. Therefore, the locking pin 66 has a position lowered with respect to that of FIG. 4, but its portion 70 still slightly protrudes into reception bore 24. In this position, when reception bar 26 of FIG. 1 is introduced into the reception bore 24, locking portion 70 can snap into a recess 36 and lock bar 26 in position. If rotary knob 60 is then rotated locking portion 70 can completely engage recess 36. It is required to rotate rotary knob 60 so far that the cam following crosspin 62 enters the groove or cam surface portion 54. When pin 62 has reached portion 54, a selflocking situation occurs because the angle of the groove or cam surface portion 54 is very small. This prevents an automatic return rotation of knob 60.

However, if locking pin 66 is actuated with the locking portion 70 not already having partly snapped into recess 36 a rotation of rotary knob 60 and, hence, a movement of locking pin 66 would cause the locking portion 70 to bear on the outer surface of the cylindrical portion 30 and not in recess 36. In this situation, cam following cross-pin 62 can be moved only within the groove or first cam surface portion 52. It cannot get into the second cam surface portion 54. Thus, this causes rotary knob 60 to be automatically rotated back to the initial position because of the action of spring 68 when locking pin 66 does not engage a recess 36. This can be ascertained by the surgeon so that any faulty operation is precluded.

While retaining bar 26 is located in place in reception bore 24 a radial pressure is exerted on portion 30 of retaining bar 26 because of the movement of locking pin 66. As a result, it is pressed against the prismatic surfaces 40, 42 so that retaining bar 26 is safely located in place.

The surgeon may look into the reception bore 24 through a window 58 and make out whether a marking or number appears in window 58 from which he can deduce with which recess 36, locking pin 66 has been brought into engagement. Since each recess 36 matches with a certain cross-bore of the locking nail (not shown), the surgeon will also know with which locking bore the target bore 18 of target apparatus 10 is aligned.

For completeness, it should also be mentioned that a tongue 80 which is opposed to sleeve portion 44 is mounted on cylindrical component 22, which tongue is placed in a recess holding portion 20 of targeting-aiming apparatus 10 and is safely mounted within such as by pins or grooves.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A targeting apparatus for a locking nail having cross-bores, the axes of which are disposed in an offset relationship from each other by predetermined distances and/or predetermined angles, comprising:
   a targeting arm having at least one target bore therein and a holding device to retain a first end of the nail;
   a retaining portion having a reception bore in which a retaining bar forming part of the holding device is guided which bar extends parallel to the targeting arm, the retaining bar has a fastener to fix the nail to a leading end of the bar, the retaining bar has several recesses in the area of the reception bore, the reception bore has associated therewith a handle having a movable locking element mounted thereon which can be caused to engage one of the recesses to locate the axial and rotational positions of the retaining bar in the reception bore, wherein the arrangement of the recesses is such that the target bore is aligned with a cross-bore of the nail when the locking element engages a recess and the handle has associated therewith means for indicating whether the locking element is in engagement with the recess or is not in engagement therewith.

2. The targeting apparatus as set forth in claim 1 wherein the handle is rotatably supported on a radially extending outer lug of the retaining portion including the reception bore and the handle actuates a radial cam follower portion which engages with a cam surface formed on a sleeve portion mounted on the retaining portion such that if the handle is rotated in a predetermined direction from an initial position in which the locking element is in its unlocking position, the locking element is moved radially with respect to the reception bore and the cam surface has a first cam surface portion defining the unlocked position and a second cam surface portion joining the first cam surface portion, wherein the engagement of the radial cam follower portion in the second cam surface portion takes place in a self-locking manner and the radial cam follower portion is biased by a spring in the direction of the first cam surface defining the unlocked position.

3. The targeting apparatus as set forth in claim 2 wherein the locking pin has an axial bore in which a helical spring first end is mounted and a second end of which is supported on the cross-bore.

4. The targeting apparatus as set forth in claim 2 wherein the radial lug is annularly cylindrical and the cam surfaces are defined by a groove in a sleeve wall and the radial cam follower portion connected to the handle engages the groove.

5. The targeting apparatus as set forth in claim 4 wherein the radial cam follower portion is defined by a cross-pin which radially extends within the groove.

6. The targeting apparatus as set forth in claim 5 wherein the cross-pin extends through a cross-bore of the locking pin.

7. The targeting apparatus as set forth in claim 1 wherein the reception bore is defined by an annularly cylindrical component which is adapted to be located in a recess of the target arm by means of a radial outer tongue.

8. The targeting apparatus as set forth in claim 7 wherein the component has at least one window through which the retaining bar can be seen.

9. The targeting apparatus as set forth in claim 1 wherein the reception bore has flat surfaces which are approximately opposed to the locking element and against which the retaining bar is pressed by the locking element.

10. The targeting apparatus as set forth in claim 1 wherein the retaining bar in the area of the recesses, has an annular groove by which the locking element can be brought into engagement with the recesses.

11. A targeting device for locating cross-bores in an implanted intramedullary nail comprising:
    a targeting arm having at least one guide bore alignable with a cross-bore in the nail and a cylindrical component extending along an axis generally perpendicular to said guide bore;
    a targeting arm positioning rod rotatably and slidably mounted within a bore of said cylindrical component, said rod fixedly mounted on an end of said intramedullary nail, said targeting arm positioning rod including a plurality of offset detents corresponding to the locations of cross-bores on said nail; and
    a selectively engageable locking element mounted on said cylindrical component moveable into and out engagement with one of the detents on said targeting arm positioning rod wherein the arrangement of the detents is such that the guide bore is aligned with a cross-bore of the nail when the locking element engages a detent.

12. The targeting device as set forth in claim 11 wherein said cylindrical component is removably mounted within a fixed bore on said targeting arm.

13. The targeting device as set forth in claim 11 wherein said detents on said targeting arm positioning rod are recesses in said rod and said detent element on said cylindrical component is moveable from a first position in said cylindrical component bore wherein said locking element extends partially into said detent recess on said targeting arm positioning rod to a second position in said bore extending fully into said detent recess.

14. The targeting device as set forth in claim 13 wherein said locking element on said cylindrical component is spring biased towards said first position.

15. The targeting device as set forth in claim 14 wherein said cylindrical component has an actuator handle mounted on an outer surface thereof, said handle engaging said detent element on said cylindrical component and being moveable against said spring biasing from a first position wherein said cylindrical component locking element is in said first position to a second position wherein said cylindrical component is in said second position.

16. The targeting device as set forth in claim 15 wherein said handle is rotatably mounted on said cylindrical component outer surface and has a cam surface thereon engageable with a cam follower on said locking element so that rotation of said handle moves said cylindrical component locking element from said first position to said second position against said spring bias.

17. The targeting device as set forth in claim 16 wherein the cam surface has a first ramp portion and a second ramp portion, the first ramp portion having a steeper angle and the second ramp portion is dimensioned to prevent said cam follower from entering said first ramp portion unless said cylindrical component locking element is manually moved into said first position.

18. A targeting device for locating cross-bores in an implanted intramedullary nail comprising:
    a targeting arm having at least one guide bore alignable with cross-bores in the nail and a cylindrical component extending along an axis generally perpendicular to said guide bore;
    a targeting arm positioning rod rotatably and slidably mounted within a bore of said cylindrical component, said rod fixedly mounted on an end of an intramedullary nail, said targeting arm positioning rod including a plurality of offset detents corresponding to the locations of said cross-bores on said nail;

a selectively engageable detent element mounted within said cylindrical component and moveable into and out of engagement with the detents on said positioning rod upon axial and/or rotational movement of the targeting arm positioning rod with respect to said cylindrical component;

a spring means for biasing said detent element from a first position partially within said bore of said cylindrical component to a second position fully within said bore and in engagement with the detents on the targeting arm positioning rod.

19. The targeting device as set forth in claim 18 wherein said cylindrical component has an actuator handle mounted on an outer surface thereof, said handle engaging said detent element on said cylindrical component and being moveable against said biasing means from a first position wherein said cylindrical component detent element is partially within the bore of the cylindrical component to a second position wherein said detent element is fully within the bore.

20. The targeting device as set forth in claim 19 wherein said handle is rotatably mounted on said cylindrical component outer surface and is engageable with a cam follower on said detent element which engages a cam surface so that rotation of said handle moves said detent element from said first position to said second position against said spring bias.

21. The targeting device as set forth in claim 20 wherein the cam surface has a first ramp portion and a second ramp portion, the first ramp portion having a small angle dimensioned to prevent said cam follower from entering said second ramp portion unless said cylindrical component detent element is moved into said second position.

* * * * *